United States Patent
Zelepouga et al.

(10) Patent No.: US 9,291,610 B2
(45) Date of Patent: Mar. 22, 2016

(54) METHOD AND APPARATUS FOR REAL-TIME MEASUREMENT OF FUEL GAS COMPOSITIONS AND HEATING VALUES

(71) Applicants: Serguei Zelepouga, Hoffman Estates, IL (US); John M. Pratapas, Naperville, IL (US); Alexei V. Saveliev, Cary, NC (US); Vilas V. Jangale, Raleigh, NC (US)

(72) Inventors: Serguei Zelepouga, Hoffman Estates, IL (US); John M. Pratapas, Naperville, IL (US); Alexei V. Saveliev, Cary, NC (US); Vilas V. Jangale, Raleigh, NC (US)

(73) Assignees: Gas Technology Institute, Des Plaines, IL (US); North Carolina State University, Raleigh, NC (US)

( * ) Notice: Subject to any disclaimer, the term of this patent is extended or adjusted under 35 U.S.C. 154(b) by 360 days.

(21) Appl. No.: 13/887,563

(22) Filed: May 6, 2013

(65) Prior Publication Data
US 2014/0326049 A1    Nov. 6, 2014

(51) Int. Cl.
| | | |
|---|---|---|
| *G01N 33/22* | (2006.01) | |
| *G01N 21/3504* | (2014.01) | |
| *G01N 21/85* | (2006.01) | |
| *G01N 21/359* | (2014.01) | |
| *G01N 21/05* | (2006.01) | |

(52) U.S. Cl.
CPC .......... *G01N 33/225* (2013.01); *G01N 21/3504* (2013.01); *G01N 21/359* (2013.01); *G01N 21/85* (2013.01); *G01N 21/05* (2013.01); *G01N 2021/8578* (2013.01); *G01N 2201/129* (2013.01)

(58) Field of Classification Search
CPC .......................... G01N 33/225; G01N 21/3504
USPC .......................................................... 702/24
See application file for complete search history.

(56) References Cited

U.S. PATENT DOCUMENTS

| | | | |
|---|---|---|---|
| 4,381,641 A * | 5/1983 | Madgavkar | F02C 3/22 252/372 |
| 4,394,239 A | 7/1983 | Kitzelmann et al. | |
| 4,397,888 A | 8/1983 | Yannopoulos et al. | |
| 5,439,580 A | 8/1995 | Akbar et al. | |
| 7,091,509 B2 | 8/2006 | Rahmouni et al. | |
| 7,764,379 B1 * | 7/2010 | McDermott | G01J 3/10 356/437 |
| 2002/0043620 A1 | 4/2002 | Tchakarov et al. | |
| 2004/0036023 A1 * | 2/2004 | Hodgkinson | G01N 21/3504 250/339.13 |
| 2006/0042354 A1 * | 3/2006 | Moritz | G01N 27/4141 73/31.06 |
| 2006/0213554 A1 | 9/2006 | Welch et al. | |
| 2006/0286423 A1 | 12/2006 | Black | |
| 2010/0228688 A1 * | 9/2010 | Little | G01N 21/359 705/413 |
| 2012/0287418 A1 * | 11/2012 | Scherer | G01N 21/61 356/51 |

OTHER PUBLICATIONS

Vilas Jangale et al.; A Real-Time Method for Determining the Composition and Heating Value of Opportunity Fuel Blends; Proc. of the ASME Internal Combustion Div. 2012 Spring Technical Conference, May 6-9, 2012, Torino, Italy.

* cited by examiner

*Primary Examiner* — Peter MacChiarolo
*Assistant Examiner* — Nathaniel Kolb
(74) *Attorney, Agent, or Firm* — Pauley Erickson & Kottis

(57) ABSTRACT

An exemplary embodiment can be an apparatus for real-time, in situ measurement of gas compositions and heating values. The apparatus includes a near infrared sensor for measuring concentrations of hydrocarbons and carbon dioxide, a mid infrared sensor for measuring concentrations of carbon monoxide and a semiconductor based sensor for measuring concentrations of hydrogen gas. A data processor having a computer program for reducing the effects of cross-sensitivities of the sensors to components other than target components of the sensors is also included. Also provided are corresponding or associated methods for real-time, in situ determination of a composition and heating value of a fuel gas.

3 Claims, 6 Drawing Sheets

Cross-sensitivity of hydrogen sensor to methane.

Cross-sensitivity of carbon monoxide sensor to ethane and butane.

$$X = \begin{bmatrix} V_{11} & V_{12} & \lambda_1 & \lambda_2 & \lambda_3 & \cdots & \lambda_m \\ & & a_{11} & a_{12} & a_{13} & \cdots & a_{1m} \\ V_{21} & V_{22} & a_{21} & a_{22} & a_{23} & \cdots & a_{2m} \\ \cdots & \cdots & \cdots & \cdots & \cdots & \cdots & \cdots \\ V_{n1} & V_{n2} & a_{n1} & a_{n2} & a_{n3} & \cdots & a_{nm} \end{bmatrix}$$

$\uparrow\uparrow$ H$_2$ and CO sensor analog outputs

NIR absorption spectra

FIG. 4

Data processing algorithm.

US 9,291,610 B2

METHOD AND APPARATUS FOR REAL-TIME MEASUREMENT OF FUEL GAS COMPOSITIONS AND HEATING VALUES

STATEMENT REGARDING FEDERALLY SPONSORED RESEARCH OR DEVELOPMENT

This invention was made with government support under contract no. DE-EE0000556 awarded by the Department of Energy. The government has certain rights in the invention.

BACKGROUND OF THE INVENTION

1. Field of the Invention

This invention generally relates to a method and apparatus for real-time, in situ measurement of fuel gas compositions and heating values. In one aspect, this invention relates to the use of infrared sensors for measuring fuel gas compositions. In one aspect, this invention relates to the use of semiconductor sensors for measuring fuel gas compositions. In one aspect, this invention relates to a method for determining the heating value of fuel gas compositions.

2. Description of Related Art

Globally increasing demand for energy and volatility in supply and pricing of natural gas and fossil fuels along with increasingly more stringent environmental restrictions, such as calls for reducing carbon emissions, have lead to growing interest in the use of alternative fuels or fuel gases from other sources such as landfill gas and producer gas, including, for example, syngas, coke oven gas, refinery gas and coalbed gas. Fuel-flexible engines, turbines, burners, and the like are being developed to better permit the use of these alternative fuels and their blends with natural gas. The reliable and efficient use of such fuel gases in engines and turbines requires proper design and operation such as to properly maintain combustion, stability, emission levels, output and efficiency. Natural gas and alternative fuels can, however, present wide variation in compositions and heating values, such as dependent on their source and treatment to which they may be subjected, whereas engines and other combustion equipment are typically designed to operate only within a specific range of fuel compositions and energy content. Thus, in order to avoid or prevent shutdowns and/or damage to such engines and equipment as well as to improve process efficiency, it is highly desirable to be able to monitor the composition of the incoming fuel and to adapt the air-fuel ratio accordingly. Further, as combustion is a very fast process, the analysis and measurement of fuel compositions and heating values must necessarily be correspondingly fast as well.

At present, gas chromatography is the most widely or commonly used method for fuel gas composition analysis and measurement. Gas chromatography, however, typically requires at least several minutes to analyze a gas sample and, thus, does not essentially provide real-time information of fuel gas properties. Calorimeters, which are used to measure the energy content of a fuel gas, have cost and response times that are similar to gas chromatographs and they only can measure the energy content of the fuel gas and not the fuel gas composition.

As used herein, the term "producer gas" refers to gas mixtures containing primarily hydrocarbons, carbon monoxide (CO), carbon dioxide ($CO_2$), hydrogen ($H_2$), and nitrogen ($N_2$). However, not all of these gases can be detected using a single inexpensive sensor. One solution to this problem is to employ a number of different sensors, each of which is intended for the detection of one or more of these gases. Known sensors suitable for use in detecting these gases are, however, problematic due to the fact that such gas sensors are generally cross-sensitive to one or more gases other than the specific target gas of the sensor. For example, as shown in FIGS. 1 and 2, palladium-based hydrogen sensors are highly cross-sensitive to methane and optical carbon monoxide sensors are cross-sensitive to ethane and butane. Thus, the use of such sensors to measure the fuel gas composition and heating value of fuel gas mixtures in real time requires proper compensation for the affects of these cross-sensitivities on the measured values produced by these sensors.

In the past few years, due to the advent of fast computing technology, multivariate regression methods, mainly, principal component regression (PCR) and partial least squares (PLS), have emerged as a promising tool for many analytical techniques. The use of near infrared (NIR) absorption spectroscopy and multivariate regression for measuring the composition and heating value of natural gas mixtures and characterizing landfill gas and synthesis gas (syngas) is known. Raman scattering can also be used to detect and measure virtually all of the components of fuel gas mixtures such as natural gas and biogas. It is also known that other physical properties of a variety of fuels ranging from gasoline and jet to diesel can be accurately predicted using multivariate modeling of NIR, FTIR (Fourier transform infrared spectroscopy), and FT-Raman measurements.

NIR sensors are significantly less expensive than Raman-based sensors. However, not all the components of conventional and alternative fuels, e.g., hydrogen, absorb light in the NIR range.

SUMMARY OF THE INVENTION

Accordingly, it is one object of this invention to provide a method and apparatus for determining the composition and heating value of fuel gas mixtures in real-time which overcomes the inaccuracies associated with the cross-sensitivity of known sensors.

This and other objects of the invention are addressed by an apparatus for real-time, in situ measurement of fuel gas compositions and heating values comprising three independent sensors—a near infrared sensor for measuring concentrations of hydrocarbons and carbon dioxide, a mid infrared sensor for measuring concentrations of carbon monoxide, a semiconductor-based sensor for measuring concentrations of hydrogen, and means for reducing the effects of the cross-sensitivities of these sensors. The apparatus of this invention may be integrated with engines, turbines, or similar combustion equipment for efficient process control and optimization.

In one particular embodiment, an apparatus for real-time, in situ measurement of gas compositions including concentrations of hydrocarbons, carbon dioxide, carbon monoxide and hydrogen gas in accordance with the invention includes a near infrared sensor for measuring light intensity in a wavelength range of 900 to 1700 nm and providing an absorption spectrum dependent on the concentrations of hydrocarbons and carbon dioxide. The apparatus also includes a mid infrared sensor for measuring light intensity in a range of in a wavelength higher than the near infrared sensor and up to 15 µm and generating an analog output directly proportional to the concentration of carbon monoxide and a semiconductor based sensor for measuring the concentration of hydrogen gas. The apparatus further includes a data processor having a computer program for reducing the effects of cross-sensitivities of the sensors to components other than target components of the sensors.

The means for reducing the effects of the cross-sensitivities of the sensors is in the form of a hardware control and data acquisition system in which the raw measurements from the sensors are arranged in a first data matrix, the fuel gas composition and heating values are arranged in a second data matrix, and the data matrices are processed using a multivariate technique selected from the group consisting of principal component regression, partial least squares regression, and partial least squares regression 2, producing models that correlate sensor measurements to component compositions and total heating value of the fuel gas.

In accordance with another aspect of the invention, there is provided a method for real-time, in situ determination of a composition and heating value of a fuel gas. Such a method in accordance with one embodiment includes measuring an amount of hydrocarbons, carbon dioxide, carbon monoxide, and hydrogen in a fuel gas using a near infrared sensor, a mid infrared sensor, and a semiconductor based sensor, producing raw measurements of said hydrocarbons, carbon dioxide, carbon monoxide, and hydrogen in the fuel gas. The raw measurements are collected in real time using a hardware control and data acquisition system. The raw measurements are arranged in a first data matrix. The fuel gas composition and heating value are arranged in a second data matrix. The data matrices are then processed sing a multivariate regression method selected from the group consisting of principal components regression, partial least squares regression, and partial least squares regression 2, thereby producing models that correlate sensor measurements to component compositions and total heating value of said fuel gas.

BRIEF DESCRIPTION OF THE DRAWINGS

These and other objects and features of this invention will be better understood from the following detailed description taken in conjunction with the drawings, wherein:

FIG. 4 is a simplified schematic representation of the arrangement of raw measurements in a data matrix X, in accordance with one embodiment of the invention;

DETAILED DESCRIPTION OF THE PRESENTLY PREFERRED EMBODIMENTS

Figure 1:
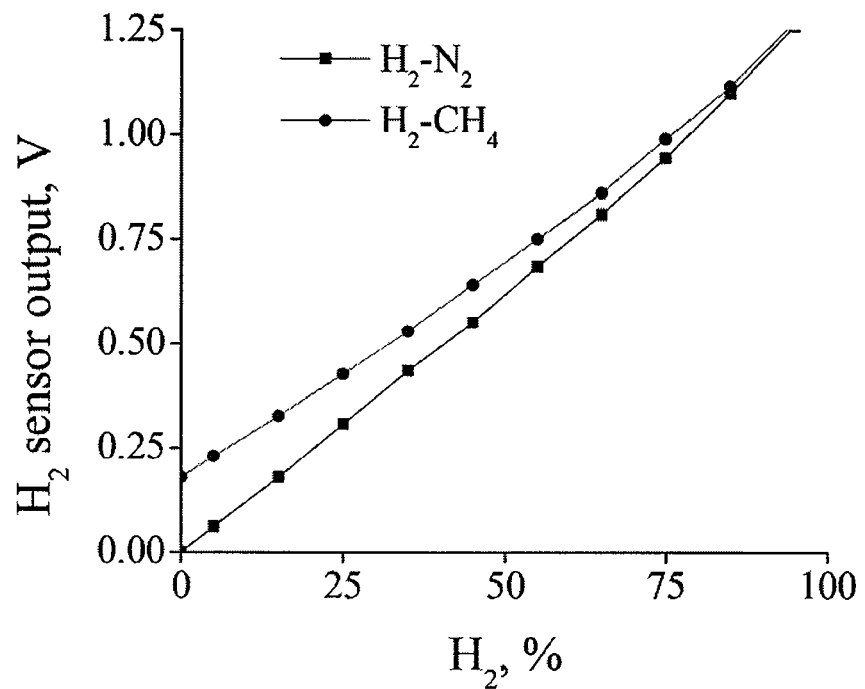
FIG. 1 is a graphical presentation of $H_2$ sensor output versus $H_2$ percentage showing the cross-sensitivity of the hydrogen sensor to methane.
Figure 2:
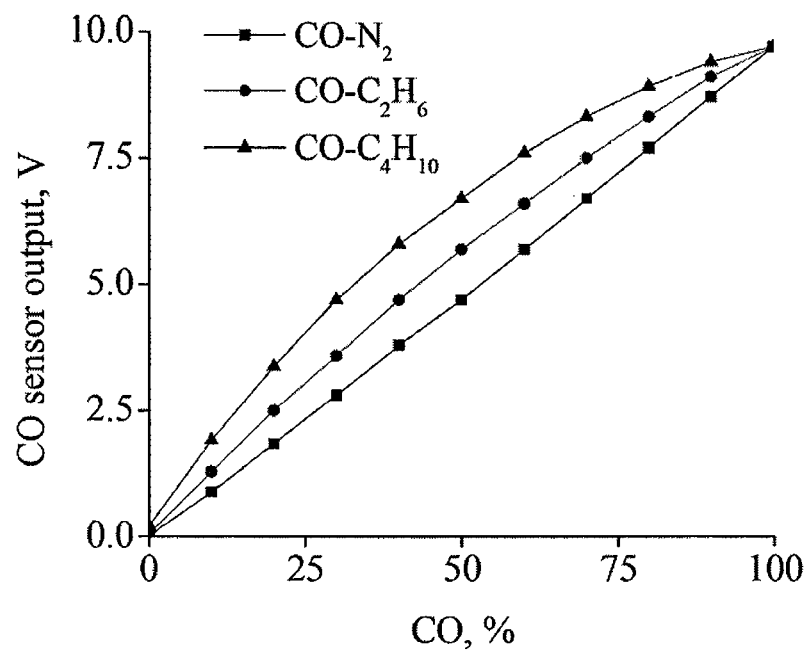
FIG. 2 is a graphical presentation of CO sensor output versus CO percentage showing the cross-sensitivity of the carbon monoxide sensor to ethane and butane.
Figure 3:
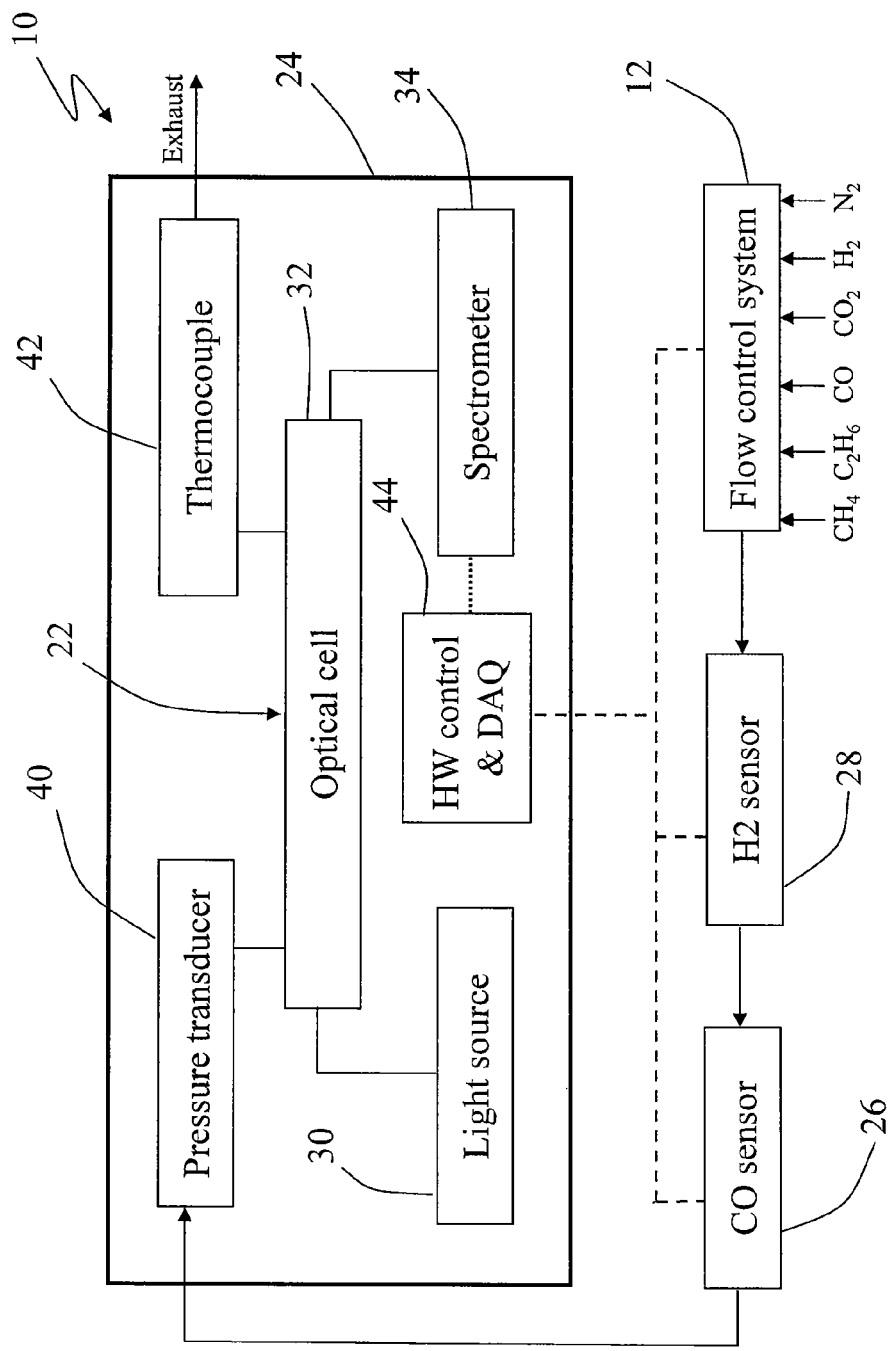
FIG. 3 is a simplified schematic diagram of a system for measuring the fuel gas composition and heating value of a fuel gas in real-time in accordance with one embodiment of this invention.

Turning to FIG. 3, there is illustrated a simplified schematic diagram of a processing system, generally designated by the reference numeral 10, for measuring the fuel gas composition and heating value of a fuel gas in real-time in accordance with one embodiment of this invention.

The processing system 10 includes a flow control system, generally designated by the reference numeral 12, whereby selected gases such as methane, ethane, carbon monoxide, carbon dioxide, hydrogen and nitrogen, for example, can desirably be introduced for analysis and processing in accordance with the invention.

The apparatus of this invention advantageously employs both optical and non-optical sensors. Thus, the system 10 includes optical sensors include a near infrared sensor 22, such as part of a gas quality sensor assembly 24 and a mid infrared sensor 26 as well as a non-optical sensor in the form of a semiconductor based sensor 28.

The near infrared sensor 22 includes a light source 30, an optical flow cell 32 and a spectrometer 34. As used herein, the term "near infrared sensor" refers to a sensor which measures light intensities at wavelengths in the range of about 900 to about 1700 nm (nanometers). This sensor is used to measure the absorption spectra of the fuel gas, the shape of which depends on the volumetric concentrations of hydrocarbons and carbon dioxide in the fuel gas.

As used herein, the term "mid infrared sensor" refers to a sensor 26 which, although technically similar to a near infrared sensor, measures light intensities in a wavelength range up to about 15 When the fuel gas flows through the flow cell of this sensor, it generates an analog output which is directly proportional to the concentration of carbon monoxide in the fuel gas. This sensor 26 can desirably be installed in-line with the flow cell of the near infrared sensor 22.

As previously stated, hydrogen does not absorb light in the infrared wavelength range, thus a semiconductor based sensor 28 is used for measuring the hydrogen concentration. The semiconductor based sensor is typically an open-flow type sensor which, when exposed to the fuel gas, generates an analog output which is directly proportional to the concentration of the hydrogen by volume in the fuel gas. This sensor can be mounted in-line or on the flow cell of the near infrared sensor 22.

The pressure and temperature of the fuel gas are desirably measured such as via a pressure transducer 40 and a thermocouple 42, such as included in the gas quality sensor assembly 24.

In operation, a multi-component fuel mixture is passed through the flow cells of the near infrared and mid infrared sensors 22 and 26, respectively, and the non-optical semiconductor based sensor 28 before being combusted for heat/power generation. Depending on the incoming fuel gas composition, the near infrared absorption spectra, hydrogen and carbon monoxide sensor outputs will vary. The measurements from these sensors are collected in real-time using a hardware control and data, acquisition system 44. The measurements are processed in a statistical algorithm using a computer and more accurate concentrations of these components and total heating value are estimated.

While the system 10 has been described above and shown in FIG. 3 as having the pressure transducer 40, the thermocouple 42 and the hardware control and data acquisition system 44 incorporated and included as components or parts of the gas quality sensor assembly 24, those skilled in the art and guided by the teachings herein provided will understand and appreciate that the broader practice of the invention is not necessarily so limited. For example, if desired, one or more of the pressure transducer, the thermocouple and the hardware control and data acquisition system can be separate and apart from the near infrared sensor such as to be otherwise appropriately incorporated in a processing system in accordance with the invention.

In accordance with one method of this invention, the raw measurements collected from the various gas sensors are systematically arranged in a data matrix X, as shown in FIG. 4. Hydrogen sensor response signals (raw analog outputs) to all the calibration mixtures are arranged in one column of X. Carbon monoxide sensor responses for (raw analog output) for each calibration mixture are arranged in another column of X. The remaining columns of the data matrix are absorbances measured at selected wavelengths.

It should be noted that the order of the columns is not important. If n is the number of calibration mixtures and m is the number of wavelengths at which absorbances are measured, then X will be a n×(m+2) matrix. Thus, the number of columns in the matrix is equal to the number of wavelengths plus the number of auxiliary sensors (two in the instant case) used, in addition to the spectrometer.

The concentrations and heating values of the mixtures are arranged in another data matrix Y. Each row of this matrix is composed of component concentrations and total heating value of the fuel gas mixture. That is, each column of the matrix is made up of concentrations of a particular component in all the mixtures. Thus, Y is a (c+1)×n matrix, where c is the number of target components to be measured. Both matrices are first mean centered. Depending on the differences in scales of measurements from the various sensors, it may be necessary to statistically scale/normalize the data. In the statistical scaling, the variables are divided by their standard deviation. The matrices are then processed using a selected multivariate calibration method to develop regression models to correlate the optical and non-optical measurements to the component concentrations and heating values. A few examples of such multivariate methods suitable for use in the method of this invention include principal components regression (PCR), partial least squares regression (PLS), and partial least squares regression 2 (PLS2), all of which are described in numerous textbooks and reference books and, thus, known to those skilled in the art. (See, for example, Naes, T. et al., "A User-Friendly Guide to Multivariate Calibration and Classification", NIR Publications, Chichester, UK (2002).)

Figure 5:
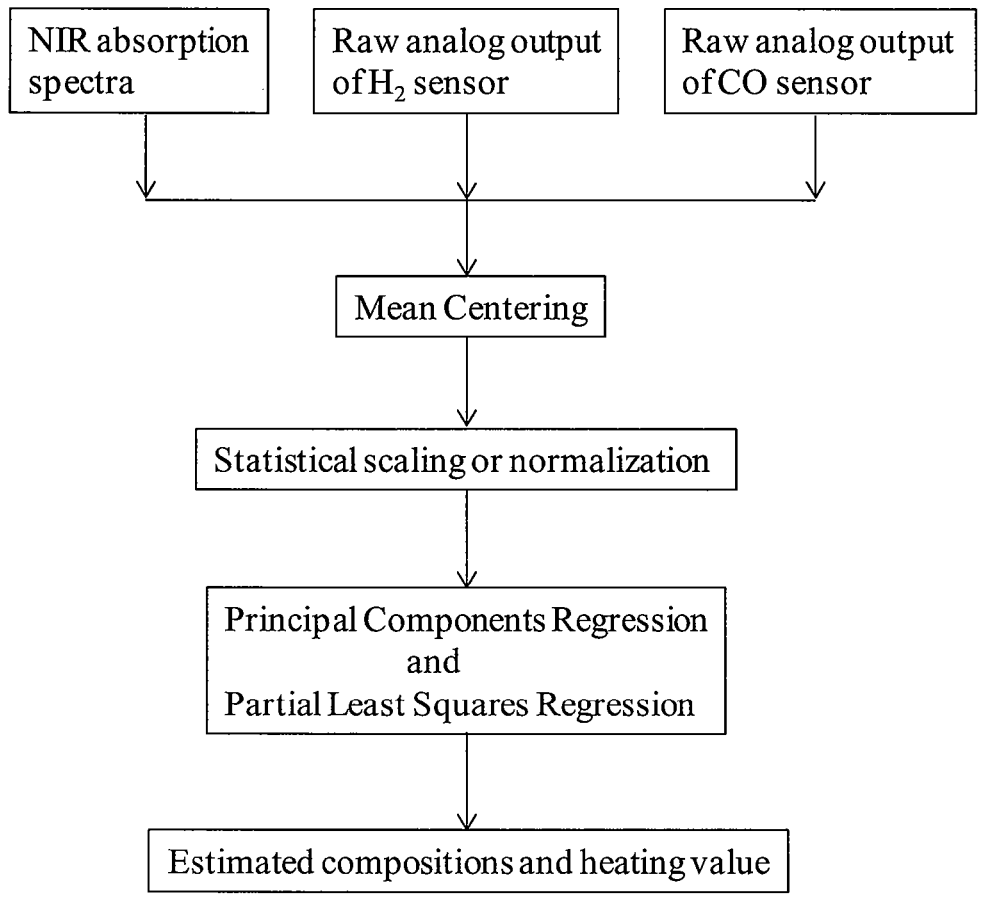
FIG. 5 is a flow diagram of a data processing algorithm/method for determining the composition and heating value of a fuel gas in real-time in accordance with one embodiment of this invention.

FIG. 5 is a flow diagram of a data processing algorithm/method for determining the composition and heating value of a fuel gas in real-time in accordance with one embodiment of this invention. The developed regression models are then utilized to estimate the compositions and heating values of unknown fuel mixtures.

According to manufacturer specifications, the degree of error in hydrogen and carbon monoxide sensors are 2% and 3%, respectively. In tests conducted on a set of 20 different fuel gas mixtures, the errors in the directly measured hydrogen and carbon monoxide concentrations were 37.5% and 1.7%, respectively. In practice, the relatively large degree of error in the directly computed hydrogen concentration is believed to be largely attributable to the hydrogen sensor being highly cross-sensitive to methane. However, through the use of methods in accordance with the invention, these errors were reduced to 0.33% and 0.84%, respectively. Thus, the concentrations of hydrogen and carbon monoxide estimated through the use of the invention are remarkably more accurate than the directly measured concentrations. Those skilled in the art and guided by the teachings herein provided will further understand and appreciate that methods and techniques in accordance with the invention can, if desired or required, be appropriately extended to analysis of more complex fuel gas mixtures, such as through the incorporation and use of additional gas sensors.

Figure 6:
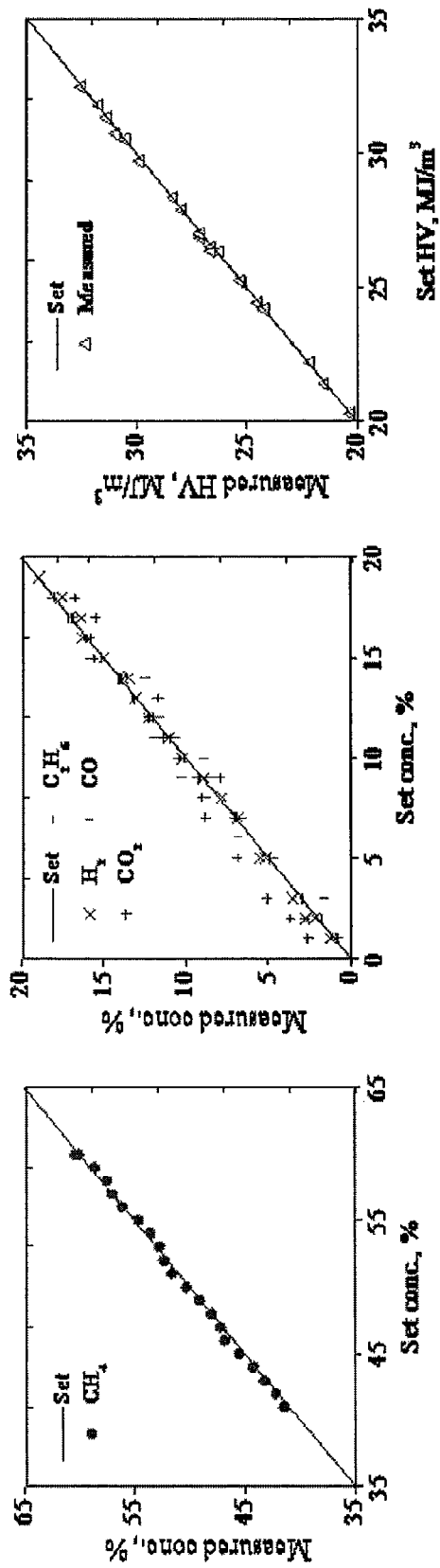
FIG. 6 is a diagram showing typical results of a laboratory validation of the method of this invention.

FIG. 6 is a diagram showing typical results of a laboratory validation of the method of this invention. Calibration and validation mixtures having pre-determined compositions were prepared using a flow control system. The target components were methane, ethane, hydrogen, carbon monoxide, and carbon dioxide. The composition and heating values of the selected mixture spanned considerably wide ranges. The results show that the estimated concentrations of each of the components are in close agreement with their actual concentrations. Thus, the invention provides methods or techniques for increased accuracy in measuring fuel compositions and heating values, which accuracy would not normally or typically be possible using direct measurements from specific gas sensors due to their non-selectivity or cross-sensitivity to other gases.

The estimated composition and heating value may be utilized to calculate other parameters important for the combustion process, such as Methane Number, Wobbe Index, and Laminar Flame Speed. This information may then be provided to an engine or a turbine control module to pre-determine the amount of air to be taken into the engine or turbine for stoichiometric combustion, thereby enhancing combustion process efficiency and reducing exhaust gas emissions.

The invention illustratively disclosed herein suitably may be practiced in the absence of any element, part, step, component, or ingredient which is not specifically disclosed herein.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

What is claimed is:

1. A method for real-time in situ determination of a composition and heating value of a fuel gas, the method comprising:
   measuring an amount of hydrocarbons and carbon dioxide in a fuel gas using a near infrared sensor producing raw measurements of said hydrocarbons and carbon dioxide in said fuel gas;
   measuring an amount of carbon monoxide in said fuel gas using a mid infrared sensor producing raw measurements of said carbon monoxide in said fuel gas;
   measuring an amount of hydrogen in said fuel gas using a semiconductor based sensor producing raw measurements of said hydrogen in said fuel gas;
   collecting all of said raw measurements in real time using a hardware control and data acquisition system;
   arranging all of said raw measurements in a first data matrix;
   arranging a composition and heating value of said fuel gas in a second data matrix; and
   processing said data matrices using a multivariate regression method selected from the group consisting of principal components regression, partial least squares regression, and partial least squares regression 2, thereby producing models that correlate sensor measurements to component compositions and total heating value of said fuel gas.

2. The method claim 1, wherein said data matrices are processed using principal components regression.

3. The method of claim 1, wherein said data matrices are processed using partial least squares regression.

* * * * *